| United States Patent [19] | [11] | 4,190,573 |
|---|---|---|
| Zwisler et al. | [45] | Feb. 26, 1980 |

[54] PROCESS FOR THE ISOLATION OF THE POLYVALENT PROTEINASE INHIBITOR

[75] Inventors: Oswald Zwisler; Gerhard Guthöhrlein; Hans-Heinrich Nau, all of Marburg an der Lahn; Helmut Rinno, Hofheim am Taunus, all of Fed. Rep. of Germany

[73] Assignee: Behringwerke Aktiengesellschaft, Marburg an der Lahn, Fed. Rep. of Germany

[21] Appl. No.: 11,679

[22] Filed: Feb. 12, 1979

Related U.S. Application Data

[63] Continuation-in-part of Ser. No. 881,527, Feb. 27, 1978, abandoned, which is a continuation of Ser. No. 713,814, Aug. 12, 1976, abandoned, which is a continuation-in-part of Ser. No. 549,432, Feb. 12, 1975, abandoned.

[30] Foreign Application Priority Data

Feb. 14, 1974 [DE]  Fed. Rep. of Germany ....... 2406971

[51] Int. Cl.$^2$ ............................................. C07G 17/00
[52] U.S. Cl. .................................. 260/112 R; 424/95; 424/177; 252/426
[58] Field of Search ................. 260/112 R, 112.5 R; 426/321; 424/95, 99, 101, 106, 110, 177; 195/31 R, 65, 66; 252/426; 210/24, 38 R

[56] References Cited

U.S. PATENT DOCUMENTS

| 3,002,887 | 10/1961 | Zilliken | 424/101 |
|---|---|---|---|
| 3,003,918 | 10/1961 | Sanders | 424/101 |
| 3,181,997 | 5/1965 | Schultz | 424/101 |
| 3,308,026 | 3/1967 | Schultz | 424/101 |
| 3,468,760 | 9/1969 | Foss | 424/99 |
| 3,558,773 | 1/1971 | Schultz | 424/95 |
| 3,682,835 | 8/1972 | Louderback | 424/101 |
| 3,809,748 | 5/1974 | Khouw | 424/95 |
| 3,855,196 | 12/1974 | Matsukawa | 424/95 |
| 3,893,890 | 7/1975 | Wurzburg | 195/104 |
| 3,912,704 | 10/1975 | Singh | 424/99 |

FOREIGN PATENT DOCUMENTS

| 1181371 | 11/1964 | Fed. Rep. of Germany | 424/95 |
|---|---|---|---|
| 1134486 | 2/1966 | United Kingdom | 424/95 |
| 1088214 | 3/1966 | United Kingdom | 424/95 |

OTHER PUBLICATIONS

Chem. Abstracts, vol. 83-3271.

*Primary Examiner*—Charles N. Hart
*Assistant Examiner*—Ernest G. Therkorn
*Attorney, Agent, or Firm*—Curtis, Morris & Safford

[57] ABSTRACT

What is disclosed is a method for the isolation of the polyvalent proteinase inhibitor from aqueous extracts of animal organs by adsorbing the inhibitor from its aqueous solutions at pH 0.5 to 10.5 on an ion exchanger containing functional sulfonate or phosphonate groups and eluting it with water or a salt solution at pH 1 to pH 13, the exchanger having a particle size from 0.03 to 0.08 mm or, in case the ion exchanger is a copolymer gel of ethene-sulfonate and acrylamide, having a particle size from 0.03 to 3 mm preferably from 0.06 to 0.3 mm.

9 Claims, No Drawings

PROCESS FOR THE ISOLATION OF THE POLYVALENT PROTEINASE INHIBITOR

This is a continuation-in-part application of co-pending application Ser. No. 881,527 filed Feb. 27, 1978 (now abandoned), which application is a continuation application of application Ser. No. 713,814 filed Aug. 12, 1976 (now abandoned), which application in turn is a continuation-in-part application of application Ser. No. 549,432 filed Feb. 12, 1975 (now abandoned).

The present invention relates to the isolation of the polyvalent proteinase inhibitor from animal organs.

The basic polyvalent proteinase inhibitor, which is also called kallikrein inhibitor, is a polypeptide well known in the art. It was first prepared by H. Kraut, E. Th. Frey, and E. Werle in 1930 [Hoppe Seylers Z. Physiol. Chem. 192, 1 (1930)]. It can be isolated from animal organs and has an outstanding importance in therapy because of its property of inhibiting trypsin, chymotryspin, the kallikreins of plasma, organs and urine, as well as plasmin.

Since the discovery of this inhibitor, a great number of processes for isolating it have become known. After extraction of organs, the inhibitor is isolated from the extract by fractionation with organic solvents such as alcohol or acetone; with the aid of various protein precipitating agents such as sulfosalicyclic acid, thiosalicyclic acid, trichloroacetic acid, metaphosphoric acid or various salts; by specific adsorption; or by chromatographic methods. However, most of these processes are unsuitable for operation on an industrial scale if it is required to obtain good yields and, additionally, to perform the process in a simple way.

A process which essentially satisfies these two requirements comprises the adsorption of the proteinase inhibitor from the organ extract onto carboxymethyl-cellulose. However, the process step of adsorption on carboxymethyl-cellulose requires using a solution of low ion strength, which can be attained only by dilution of the organ extract. In addition to this disadvantage of having to operate with large volumes and a large amount of ion exchanger, the filterability of the strongly swelling carboxymethyl-cellulose presents a technically difficult problem which is all the more serious in the regeneration of the exchanger, which regeneration must be carried out in the alkaline pH-range. In view of the known basic properties of the polyvalent proteinase inhibitor, those skilled in the art would expect that it must be possible to isolate this substance using acid ion exchangers, other than carboxylmethyl cellulose, which have the form of a resin and which do not have the above-described disadvantages. However, the methods described in the literature in this respect proved very unsatisfactory [B. Kassell et al., J. Biol. Chem. 238, 3274 (1963)]. A large amount of exchanger resin is required for the adsorption of the inhibitor but either the yields are relatively poor and the product obtained has an unsatisfactory purity, or a very pure product is prepared using considerably expensive fractionation measures without regard to the yield, which would be inapplicable on an industrial scale.

It has now been found that cation exchangers which carry sulfonic acid groups or phosphonic acid groups as functional groups and which have a defined particle size are particularly suited for the isolation of the polyvalent proteinase inhibitor.

The particle size of the ion exchanger is important. If the particles are too large, adsorption is only poor. Too small particles, on the other hand, will not result in a further increase of the amount of inhibitor adsorbed thereon. Thus the preferred range of particle size for the ion exchangers is between 0.03 and 0.08 mm. In the case of some special ion exchangers such as copolymers of ethane sulfonic acid and acrylamide, the upper limit of the particle size range can be extended up to about 3 mm, the preferred range for these exchangers being between 0.06 and 0.3 mm.

The commercially-available polyphenol-ω-sulfonic acid ion exchangers and polystyrene-sulfonic acid resins, in particular those whose capacity is increased because of a macroporous structure, or polystyrene-phosphonic acid resins are well suited for use in the process of the invention. A grain size for these ion exchangers of about 0.03 to 0.08 mm has shown to be particularly advantageous.

Copolymer gels of ethene-sulfonate and acrylamide may also be used with advantage as an adsorbant. For example, a gel of this kind, which can be prepared according to a known process as described in Example 1 of the present specification, is a copolymer of ethene-sulfonic acid and acrylamide in a weight proportion of about 20:1 to 2:1, preferably 8:1 to 3:1, which is cross-linked with 1 to 15% by weight of formaldehyde. The grain size suitable for the adsorption of the proteinase inhibitor on these exchangers is not only in the range from 0.03 to 0.08 mm but extends up to 3 mm, the preferred range being between 0.06 and 0.3 mm.

The ion exchanger types of the present invention are distinguished from carboxymethyl-cellulose by a considerably higher adsorptive capacity.

Furthermore, the speed of filtration can be significantly increased using the resins according to the invention, as compared with that using carboxymethyl-cellulose, both for the separation of unadsorbed material and for the elution of the inhibitor. Since the through-flow speed of solutions is also not impeded in the alkaline range, the ion exchangers mentioned can be easily regenerated after elution of the inhibitor. The exchangers may be used several times for the isolation of the polyvalent proteinase inhibitor. This can be effected according to the batch method or according to the column method.

Accordingly, the object of the present invention is a process for the isolation of the polyvalent proteinase inhibitor from its aqueous solutions, preferably from an aqueous extract of animal organs, preferably from bovine lungs, which comprises adsorbing the inhibitor on an ion exchanger resin having functional sulfonic acid groups or phosphonic acid groups and having a particle size as defined above at pH-values of from 0.5 to 10.5, preferably pH-values of from 7.5 to 9.5, separating the adsorbant and subsequently eluting it with aqueous saline solutions at pH-values of 1 to 13, preferably pH-values of from 10 to 12.5. In the proximity of pH 12.5, the addition of a salt may be omitted, whereas with decreasing pH-value increasing amounts of salt are to be added in order to augment the elutive capacity. If an ethene-sulfonate/acrylamide copolymer gel is used, about 10% of sodium chloride are added to the eluting medium at a pH value of 3, for example. If polyphenol-ω-sulfonic acid ion exchangers, or polystyrene-phosphoric acid resins, or polystyrene-sulfonic acid resins are used, the elution may be carried out, for example at pH 7.0, with the addition of about 20% of sodium chloride or such amounts of another salt as provide a comparable elution capacity. It must be taken into consideration that with these types of exchangers the inhibitor may precipitate when elution is performed at pH values below 5 because of the higher salt concentrations required for elution. This must be compensated for by an increased elution volume in order to keep yield losses as low as possible.

It is of advantage to use a prepurified extract of animal organs as the starting material for the adsorption of the proteinase inhibitor.

The inhibition of plasmin using casein as the substrate may be used for determining the proteinase inhibitor isolated according to the invention. This test determines how much the enzymatic activity of a plasmin, previously determined according to the method described by L. F. Remmert and P. P. Cohen in J. Biol. Chem. 181, 431 (1949), is reduced by a quantity of added inhibitor. The inhibition of a plasmin unit is defined as an antiplasmin unit (APU). With a view to the specific activity of the proteinase inhibitor, the APU/ml are referred to an extinction value of the solution of the inhibitor of 1.0, measured at a wave length of 280 mm. Consequently, referred to APU/mg of nitrogen, a purification factor of 20 to 35 is attained according to the process of the invention.

The eluate obtained according to the invention may be further purified by gel chromatography, whereupon the inhibitor is obtained in high purity and with good yield. Thus, an inhibitor of about 170 APU/ml at $\Delta E_{280}=1.0$ can be obtained. This purity of the polyvalent proteinase inhibitor permits its therapeutic use in humans.

The following Examples illustrate the invention.

EXAMPLE 1

A. Preparation of a copolymer of ethene-sulfonate and acrylamide:

80 parts by weight of a 25% aqueous solution of the Na-salt of ethene-sulfonic acid were adjusted to a pH of 6.9 with 40% $H_2SO_4$. Then, 5.3 parts by weight of acrylamide were dissolved in this solution and the whole was heated to 45° C. Polymerization was initiated by the addition of 0.425 parts by weight of ammonium peroxide disulfate and 0.085 part by weight of sodium bisulfite. The batch heated up to 98° C. In order to complete the polymerization, 0.0425 part by weight of ammonium peroxide disulfate and 0.0085 part by weight of sodium bisulfite were added, the whole was stirred for 2 hours at 85° C. and then cooled.

B. Cross-linking with formaldehyde and thermal after treatment:

13.6 parts by weight of a 28% formaldehyde solution were added to the solution of copolymer and allowed to stand for 15 hours at 25° C. The gel obtained was dried at 80° C. under reduced pressure and the dry product was heated for 30 minutes at 150° C. It was then ground and sieved. The fraction having a grain size of 0.06 to 0.3 mm was found to be especially suitable for the isolation of the polyvalent proteinase inhibitor. Before use, the cross-linked product was swollen by washing with desalted water and freed from water-soluble by-products.

C. Isolation of proteinase inhibitor using the copolymer resins:

33 kg of the wet ethene-sulfonate/acrylamide copolymer gel (prepared as described above) were added to 1650 l of a crude extract of bovine lung tissue which contained $12 \times 10^6$ antiplasmin units. The mixture was stirred for 30 minutes and then allowed to stand for 30 minutes to permit sedimentation of the adsorbant. 1250 l of the supernatant could then be decanted off. In order to remove the residual supernatant, the adsorbant was filtered off. Elution of the proteinase inhibitor was effected with 120 l of deionized water, the pH-value of the suspension having been adjusted to 12.5 by means of concentrated sodium hydroxide solution. The eluate contained 95% of the quantity of inhibitor present in the extract in a purity of 60 APU/ml at $\Delta E_{280}=1.0$. The eluate obtained in the aforementioned manner could advantageously be freed from higher molecular weight impurities by gel chromatography, for example on "Sephadex ® G-50" (Deutsche Pharmacia, Frankfurt/M.). Thereby, the active substance was obtained with a purity of 140–200 APU/ml at $\Delta E_{280}=1.0$ and in a yield of more than 50% referred to the raw extract.

If desired or required, the proteinase inhibitor so obtained may be subjected to a process for removing pyrogens, adjusted to a therapeutically usual concentration of 250 APU/ml, filtered under sterile conditions and filled into ampules.

In this form, the proteinase inhibitor may be administered parenterally, in particular intravenously.

EXAMPLES 2 TO 13

5 liters each of a bovine lung tissue raw extract containing about 6 APU/ml were combined with different amounts of various ion exchangers and worked up essentially as described in Example 1 (C). The following compilation shows, by way of example, some of the tests carried out.

| | Ion Exchanger | | | Reaction Conditions | | | Proteinase Inhibitor |
|---|---|---|---|---|---|---|---|
| Example | Designation | Functional Group | Quantity g/l | Ads. at pH | Eluant | Yield % | Purity APU/ml at $E_{280}=1$ |
| 2 | Copolymer gel acc. to Example 1 | Sulfonic acid | 20 | 8.5 | Water/ 10% NaCl pH 3.0 | 92 | 60 |
| 3 | Copolymer gel acc. to Example 1 | Sulfonic acid | 20 | 8.5 | Water pH 12.5 | 81 | 70 |
| 4 | Copolymer gel acc. to Example 1 | Sulfonic acid | 20 | 8.5 | Water/ 10% NaCl pH 4.5 | 82 | 71 |
| 5 | Copolymer gel acc. to | Sulfonic acid | 20 | 4.5 | Water pH 12.5 | 92 | 10 |

-continued

| Example | Ion Exchanger Designation | Functional Group | Quantity g/l | Reaction Conditions Ads. at pH | Eluant | Yield % | Proteinase Inhibitor Purity APU/ml at $E_{280}=1$ |
|---|---|---|---|---|---|---|---|
| 6 | Copolymer gel acc. to Example 1 | Sulfonic acid | 20 | 4.5 | Water/ 10% NaCl pH 4.5 | 85 | 13 |
| 7 | Bio-Rex® 40[1] | Sulfonic acid | 2 | 8.5 | Water pH 12.5 | 90 | 53 |
| 8 | Bio Rex® 40[1] | Sulfonic acid | 2 | 8.5 | Water/ 20% NaCl pH 7.0 | 65 | 52 |
| 9 | AG®-MP-50[3] | Sulfonic acid | 4 | 8.5 | Water pH 12.5 | 94 | 32 |
| 10 | Bio-Rex® 63[2] | Phosphonic acid | 6 | 8.5 | Water pH 12.5 | 75 | 53 |
| 11 | Copolymer gel acc. to Example 1 | Sulfonic acid | 20 | 0.5 | Water pH 12.5 | 100 | 8.2 |
| 12 | Copolymer gel acc. to Example 1 | Sulfonic acid | 20 | 3.0 | Water pH 12.5 | 92 | 9.1 |
| 13 | Copolymer gel acc. to Example 1 | Sulfonic acid | 20 | 10.0 | Water pH 12.5 | 51 | 74.9 |

[1] Bio-Rex 40 is an ion-Exchanger manufactured by Bio-Rad Laboratories, Richmond, California, U.S.A., consisting of a strongly acidic sulfonated phenolic resin containing omega sulfonic acid exchange groups on a phenolic lattice (Catalogue X 1972 of Bio-Rad Laboratories, page 4).
[2] Bio-Rex 63 is an intermediate acid resin containing phosphonic acid difunctional groups on a styrene-divinylbenzene lattice, manufactured by Bio-Rad Laboratories (ibid, page 4).
[3] AG MP-50 is a macroporous resin the matrix of which is a styrene-divinylbenzene copolymer and the ion exchange groups are sulfonic acid groups (Catalogue X 1972 of Bio-Rad Laboratories, page 8).

We claim:

1. In a method for isolating polyvalent proteinase inhibitor, obtained by the aqueous extraction of animal organs, from an aqueous solution of said inhibitor, which method comprises contacting said aqueous solution with an acid ion exchanger to adsorb said inhibitor thereon and subsequently desorbing said inhibitor from said acid ion exchanger, the improvement wherein said aqueous solution of said inhibitor is contacted at a pH from 0.5 to 10.5 with an ion exchanger selected from the group consisting of polyphenol-ω-sulfonic acid, polystyrene sulfonic acid, and polystyrene phosphonic acid and having a particle size between 0.03 and 0.08 mm, or with an ion exchanger which is a copolymer of ethene sulfonate and acrylamide having a particle size between 0.03 and 3 mm, whereby said inhibitor is adsorbed on said ion exchanger, and said inhibitor is then eluted from said ion exchanger with water or a salt solution at a pH from 1 to 13.

2. A method as in claim 1 wherein said ion exchanger is a polystyrene phosphonic acid.

3. A method as in claim 1 wherein said ion exchanger is a polyphenol-ω-sulfonic acid.

4. A method as in claim 1 wherein said ion exchanger is a polystyrene sulfonic acid.

5. A method as in claim 1 wherein said ion exchanger is a copolymer gel of ethene sulfonate and acrylamide.

6. A method as in claim 5 wherein said ion exchanger is a copolymer of ethene sulfonate and acrylamide in a weight ratio between 20:1 and 2:1, said copolymer is further cross-linked with 1 to 15 percent by weight of formaldehyde, and said ion exchanger has a grain size between 0.06 and 0.3 mm.

7. A method as in claim 5 wherein the inhibitor adsorbed on said ion exchanger is eluted therefrom with 10 percent sodium chloride solution at a pH of 3.0.

8. A method as in claim 1 wherein said inhibitor is eluted from said ion exchanger with water at a pH of about 12.5.

9. A method as in claim 1 wherein said ion exchanger is a member selected from the group consisting of polyphenol-ω-sulfonic acid, polystyrene sulfonic acid, and polystyrene phosphonic acid, and said inhibitor is eluted therefrom with a 20 percent sodium chloride solution at a pH of 7.0.

* * * * *